(12) United States Patent
Parikh et al.

(10) Patent No.: US 12,290,504 B2
(45) Date of Patent: May 6, 2025

(54) AQUEOUS FORMULATIONS OF TOPIRAMATE

(71) Applicant: TaP Pharmaceuticals AG, Baar (CH)

(72) Inventors: Nilesh Parikh, Irvine, CA (US); William Hite, Winchester, CA (US); Kartik Shah, Mumbai (IN)

(73) Assignee: TaP Pharmaceuticals AG, Zug (CH)

( * ) Notice: Subject to any disclaimer, the term of this patent is extended or adjusted under 35 U.S.C. 154(b) by 0 days.

(21) Appl. No.: 18/133,349

(22) Filed: Apr. 11, 2023

(65) Prior Publication Data

US 2024/0342132 A1 Oct. 17, 2024

(51) Int. Cl.
| | | |
|---|---|---|
| *A61K 31/36* | (2006.01) | |
| *A61K 9/00* | (2006.01) | |
| *A61K 9/08* | (2006.01) | |
| *A61K 47/10* | (2017.01) | |

(52) U.S. Cl.
CPC ............ *A61K 31/36* (2013.01); *A61K 9/0053* (2013.01); *A61K 9/08* (2013.01); *A61K 47/10* (2013.01)

(58) Field of Classification Search
CPC .................................................... A61K 31/36
See application file for complete search history.

(56) References Cited

U.S. PATENT DOCUMENTS

| | | |
|---|---|---|
| 6,294,192 B1 | 9/2001 | Patel et al. |
| 11,197,823 B2 | 12/2021 | Sudhakar et al. |
| 11,197,825 B2 | 12/2021 | Sudhakar et al. |
| 2006/0270611 A1 | 11/2006 | Dries et al. |
| 2021/0169844 A1 | 6/2021 | Tu et al. |
| 2023/0240985 A1* | 8/2023 | Pandey .................. A61K 31/35 514/454 |

FOREIGN PATENT DOCUMENTS

| | | |
|---|---|---|
| GB | 2594242 A | 10/2021 |
| WO | 2005048981 A1 | 6/2005 |
| WO | 2020053662 A2 | 3/2020 |

OTHER PUBLICATIONS

Paramar et al. HPTLC Method for Estimation of Topiramate in Solubility Studies, Diffusion Studies, Plasma, Brain Homogenate and Pharmaceutical Formulation. Journal of Chromatographic Science, 2016, vol. 54, No. 7, 1105-1114.
Azurity Pharmaceuticals, Inc. Eprontia package insert.

* cited by examiner

*Primary Examiner* — Sarah Alawadi
(74) *Attorney, Agent, or Firm* — John Burr

(57) ABSTRACT

Certain embodiments of the present disclosure provide storage-stable, aqueous pharmaceutical formulations, suitable for oral administration, that contain a therapeutically effective amount of that is from 2% w/v to 7.5% w/v topiramate, from 45% w/v to 75% w/v PEG 400, from 6% w/v to 12% w/v water, balance glycerol. In some embodiments, such formulations further comprise a sweetener (e.g., sucralose) and/or a flavorant (e.g., berry flavor).

18 Claims, No Drawings

AQUEOUS FORMULATIONS OF TOPIRAMATE

FIELD

The instant disclosure provides aqueous pharmaceutical formulations, suitable for oral administration, that comprise topiramate and that exhibit advantageous stability properties, and methods of making and using same.

BACKGROUND

Carbonic anhydrase inhibitors have a variety of established clinical uses, such as in treatment of glaucoma, altitude sickness, ulcers, idiopathic intracranial hypertension, osteoporosis, type II diabetes, tobacco dependence, obesity, eating disorders (e.g., binge eating and antipsychotic-induced weight gain), and neurological disorders (e.g., depression, mania, bipolar disorder, and borderline personality disorder) and as a diuretic and antiepileptic. Carbonic anhydrase inhibitors include acetazolamide, methazolamide, dorzolamide, brinzolamide, dichlorphenamide, sultiame, and topiramate. Topiramate is the active pharmaceutical ingredient in EPRONTIAR (topiramate) oral solution, which is indicated as an initial monotherapy for the treatment of partial-onset or primary generalized tonic-clonic seizures and as adjunctive therapy for the treatment of partial-onset seizures, primary generalized tonic-clonic seizures, or seizures associated with Lennox-Gastaut syndrome; and for preventive treatment of migraine.

Topiramate is a lactam containing compound and chemically described as 2,3:4,5-Di-O-isopropylidene-β-D-fructopyranose sulfamate and has the molecular formula $C_{12}H_{21}NO_8S$ and a molecular weight of 339.36. The chemical structure of topiramate is:

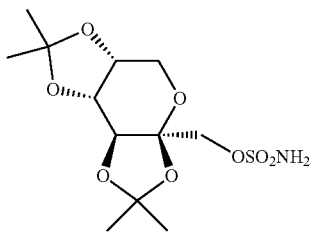

Patent Cooperation Treaty publication WO 2005/048981 (the "'981 publication") teaches dosage forms for controlled release delivery of topiramate. The dosage forms comprise a semipermeable wall, a drug layer, and an expandable layer. The semipermeable wall is permeable to the passage of an exterior biological fluid and substantially impermeable to the passage of drug formulation and surrounds and forms a compartment comprising a plurality of layers. The plurality of layers comprises at least one drug layer comprising topiramate solubilized in a nonaqueous liquid carrier and at least one expandable layer. The liquid carrier comprises a lipophilic carrier, a surfactant, or a hydrophilic solvent, or a combination thereof. The '981 publication teaches that its nonaqueous liquid carrier can contain a certain amount of aqueous liquid (for example, about 10 or 20% aqueous liquid) as long as the liquid carrier is predominantly non-aqueous. The '981 publication teaches that selection of the liquid carrier is based upon drug-excipient compatibility, and physical and chemical stability of the compounds.

United States Patent Application Publication 2006/0270611 (the "611 publication") teaches that liquid preconcentrate compositions comprising topiramate or a pharmaceutically acceptable addition salt thereof as active ingredient and an organic solvent, the preconcentrate compositions having a low water content subsequently mixed with aqueous medium. The '611 publication teaches that topiramate is sensitive to hydrolysis in an aqueous medium and therefore cannot be formulated as a conventional aqueous solution for oral use. Such an aqueous solution would have a very limited shelf life. By formulating topiramate as a liquid non-aqueous preconcentrate composition, in particular a liquid preconcentrate composition with a low water content, more in particular a liquid preconcentrate composition in an essentially organic solvent, a formulation can be provided with an acceptable shelf life. The '611 publication teaches that a low water content means that the concentration of water in the composition is preferably about 5% by weight or less, more preferably 2.5% by weight or less, even more preferably about 1% by weight or less or that the composition is substantially free of water. And that substantially free of water in this context means that the concentration of water in the composition is preferably about 0.3% by weight or less, even more preferably about 0.2% by weight or less. The '611 publication teaches five working examples of its formulations, four of which contain no water and one (i.e., Composition A) contains a calculated 0.6% w/w water. The ingredients, and their quantities, of the '611 publication's Composition A is reproduced in Table A

TABLE A

| Ingredient | Quantity |
| --- | --- |
| topiramate (free acid) | 3.0 kg |
| methyl parahydroxybenzoate | 2.16 kg |
| propyl parahydroxybenzoate | 0.24 kg |
| sucralose | 3.0 kg |
| grenadine flavour | 0.48 kg |
| masking flavour, in particular masking flavour 11031-31 (Givaudan) | 0.24 kg |
| sodium hydroxide | q.s. a pH 7 (reflects pH value of the composition upon reconstitution) |
| purified water | 0.75 L |
| polyethylene glycol | 50.0 kg |
| glycerol | q.s. ad 100 L |

The '611 publication teaches that synthesis of its Composition A, 100-liter batch size, involved a series of initial steps of combining and mixing excipients and topiramate. The resultant solution was stirred under an inert atmosphere, preferably $N_2$; and then, also under inert atmosphere, filtered (25 μm) and filled (15 ml) into glass bottles (100 ml) to form a preconcentrate. The preconcentrate was, prior to administration, diluted in a ratio of 1 part of preconcentrate and 5 parts of purified water. The parts are preferably volume parts. In contrast, the process for preparing the four water-free topiramate preconcentrate-formulations taught by the '611 publication does not involve any step or aspect conducted under inert atmosphere.

U.S. Pat. No. 11,433,046 (the "'046 patent") teaches compositions for the liquid oral administration of topiramate and its salts. The '046 patent teaches topiramate compositions that are substantially anhydrous and comprise one or more organic solvents, and that such compositions are stable at room temperature for at least two years and without need for dilution. The '046 patent teaches that topiramate is not stable in aqueous solution and therefore has been heretofore formulated primarily in solid dosage forms such as capsules and tablets from which water can easily be excluded. The '046 patent states that it has been discovered that in accordance with its disclosure that the exclusion of any added water, and/or the removal of water, from the compositions confers topiramate stability even in the presence of atmospheric oxygen. The '046 patent states that the exclusion of water from its compositions greatly reduces hydrolysis and oxidation due to atmospheric oxygen. And that it provides a ready-to-use oral liquid solution which is stable at room temperature, and which is stable even in the presence of atmospheric oxygen at room temperature for up to two years. The '046 patent teaches that "substantially anhydrous" is intended to mean that a composition does not contain any added water, other than traces of water that might exist in the various components of the formulation as a consequence of the processes of manufacture. The '046 patent teaches that its substantially anhydrous compositions contain less than about 0.5% w/w total water, including any trace water present in the various components of the formulation. Or that the total amount of water present in the composition is about 0.35% w/w or less; from about 0.001% to about 0.35% w/w; or from about 0.01% to about 0.3% w/w; or from about 0.1% to about 0.3% w/w, or from about 0.15% to about 0.25% w/w; or from about 0.2% to about 0.25% w/w, or about 0.22% w/w; or the composition is devoid of detectable water.

SUMMARY

Certain embodiments of the present disclosure provide aqueous pharmaceutical formulations that are suitable for oral administration and that contain from 2% w/v to 7.5% w/v, or from 2.5% to 5% w/v topiramate or a pharmaceutically acceptable salt thereof; from 45% w/v to 75% w/v polyethylene glycol 400 from 6% w/v to 12% w/v water; and balance glycerol. Such formulations exhibit insignificant topiramate assay drop after six months at 40° C. and 75% relative humidity and otherwise standard laboratory conditions. In some of such formulations, the topiramate assay drop is from 2% to 10%, alternatively from 3% to 10% or from 5% to 10%. Some of such formulations comprise 6% w/v water, 8% w/v water, or 10% w/v water. In some embodiments, the formulations further contain at least one of from 0.01% w/v to 2.0% w/v of a sweetener and from 0.01% w/v to 2.0% w/v of a flavorant. In some embodiments, the sweetener that is a sucralose and the flavorant is a berry.

Certain embodiments of the present disclosure provide aqueous pharmaceutical formulations, suitable for oral administration, that consist essentially of 2.5% w/v or 5% w/v topiramate or a pharmaceutically acceptable salt thereof; 50% w/v or 70% w/v polyethylene glycol 400; from 6% w/v, 8% w/v, or 10% w/v water; at least one of from 0.01% w/v to 2.0% w/v of a sweetener and from 0.01% w/v to 2.0% w/v of a flavorant; and balance glycerol. Such formulations exhibit insignificant topiramate assay drop after six months at 40° C. and 75% relative humidity and otherwise standard laboratory conditions. In some of such formulations, the topiramate assay drop is from 2% to 10%, alternatively from 3% to 10% or from 5% to 10%. In some of such formulations, the sweetener is a sucralose and the flavorant is a berry. Certain embodiments of the present disclosure provide methods of treating one or more of conditions: (i) partial-onset tonic-clonic seizures, (ii) primary generalized tonic-clonic seizures, or (iii) seizures associated with Lennox-Gastaut syndrome, comprising orally administering a formulation of the disclosure to a subject presenting one or more of conditions (i), (ii), and (iii).

DETAILED DESCRIPTION

The present disclosure provides aqueous pharmaceutical formulations of topiramate that are suitable for oral administration. Such topiramate formulations comprise 6% w/w or more water, preferably 10% w/w water, and advantageously exhibit desirable topiramate storage stability properties and simultaneously desirable finished dosage form viscosity that allows for enhanced dosing accuracy. In certain embodiments of the present disclosure, aqueous topiramate formulations exhibit desirable topiramate storage stability properties, for example demonstrating stability over six months at 40° C. and 75% relative humidity, or in a similar accelerated stability test.

Formulations as disclosed herein can be provided in pourable dosage forms that are not encapsulated.

Formulations of the disclosure are useful for treating treatment of glaucoma, altitude sickness, ulcers, idiopathic intracranial hypertension, osteoporosis, type II diabetes, tobacco dependence, obesity, eating disorders (e.g., binge eating and antipsychotic-induced weight gain), neurological disorders (e.g., depression, mania, bipolar disorder, and borderline personality disorder), migraine, partial-onset or primary generalized tonic-clonic seizures, and partial-onset seizures, primary generalized tonic-clonic seizures, or seizures associated with Lennox-Gastaut syndrome; and for preventive treatment of migraine.

Formulations as disclosed herein can "comprise" a list of ingredients, such list then being open to inclusion of further unspecified ingredients. Alternatively, formulations as disclosed herein can "consist of" a list of ingredients, meaning that the formulations include only the listed ingredients. Or, formulations as disclosed herein can "consist essentially of" the listed ingredients, meaning that the formulations include all of the listed ingredients, and may include as well any further ingredients that do not materially affect the utility of the formulation. Such utility for the purposes of the present disclosure is maintenance of a high concentration of topiramate in a solution phase in a liquid formulation.

Formulations as disclosed herein may consist of topiramate, or a pharmaceutically acceptable salt thereof, glycerol and a PEG as these are described, and in the proportions disclosed, herein below. Formulations as disclosed herein may consist of topiramate or a pharmaceutically acceptable salt thereof, glycerol and a polyethylene glycol (PEG) as these are described, and in the proportions disclosed, herein below, and further any one or more of a flavorant, a pH adjusting agent and/or a buffer, a polymer, a surfactant, a tonicity agent and a preservative, as these are described, and in the proportions disclosed, herein below.

In some formulations of the disclosure, the proportion, of the total amount of topiramate in the formulation, that is in the solution phase thereof can be 30%, 35%, 40%, 45%, 50%, 55%, 60%, 65%, 70%, 75%, 80%, 85%, 90%, 95%, 96% 97%, 98%, 99%, or 100% or ranges between two of those percentages.

In some embodiments, formulations of the present disclosure contain topiramate, at concentrations in the overall formulation, of 5 mg/ml, 10 mg/ml, 15 mg/ml, 20 mg/ml, 25 mg/ml, 30 mg/ml, 35 mg/ml, 40 mg/ml, 45 mg/ml, 50 mg/ml, 55 mg/ml, 60 mg/ml, 75 mg/ml, or 100 mg/ml, or ranges between any two of those concentrations.

In some embodiments, a formulation of the disclosure can consist of the topiramate, PEG, and glycerine. In some embodiments, a formulation of the disclosure can consist of the topiramate, PEG, and glycerol and one or more of a sweetener, flavorant, polymer, surfactant, tonicity agent and preservative as described below.

PEGs useful in formulations of the disclosure include those having a molecular weight of 200, 300, 400, 500, 600, 1000, 2000, 3000, 5000, or 8000 or in a range between any two of those molecular weights. Formulation of the disclosure may have a PEG content, in weight to weight (w/w) or weight to volume (w/v) proportions of the overall formulation, of 25%, 30%, 35%, 40%, 45%, 50%, 55%, 60%, 65%, 70%, 75%, or 80% or in a range between any two of those PEG content proportions. The formulations may comprise combinations of PEG, in amounts that individually or in aggregate achieve(s) the stated tonicity proportions.

Glycerols useful in formulations of the disclosure include glycerol USP Grade (1,2,3-Propanetriol), a colorless, odorless liquid available at a minimum 96.0% or a minimum 99.5% glycerol by assay. Commercially available glycerols include 99.9% glycerol by Puratin, 99.7% glycerol by Optim, 100% glycerol by JT Baker, 99.5% glycerol by MP Biomedicals, 99.4% glycerol by Honeywell, 99.8% glycerol by VWR Scientific, 99% glycerol by Spectrum, 100% glycerol by Millipore Sigma, 99% glycerol by Bean Town Chemical, 99.9% glycerol by ThermoFisher Scientific Chemicals, 99.8% glycerol by Arcos Chemicals, 99.8% glycerol by VWR International. Also useful in formulations of the disclosure are glycerol esters that include glycerol 2 ethyl hexyl oleate, glycerol trioleate, glyceryl dioleate, glyceryl monooleate, and glyceryl monotallate. Formulations of the disclosure may have a glycerol content, in weight to weight (w/w) or weight to volume (w/v) proportions of the overall formulation, of 2.5%, 5%, 7.5%, 10%, 12.5%, 15%, 20%, 30%, 35%, 40%, 45%, 50%, 55%, 60%, 65%, 70%, 75%, or 80% or in a range between two of those glycerol content proportions.

In some embodiments, formulations of the disclosure can include a sweetener. Sweeteners useful in the formulations of the present disclosure include acesulfame-K, advantame, alitame, aspartame, brazzein, carrelame, curculin, cyclamic acid, corn syrup (e.g., high fructose corn syrup), cyclamate, dihydrochalchone, erythritol, fructose, galactose, glucose, glycine, glycyrrhizic acid, hydrogenated glucose syrup, hydrogenated starch hydrolysate, isomalt, lactitol, lactose, mabilin, miraculin, maltitol, maltodextrin, maltose, monatin, mannitol, mannose, mogrosides, monellin, neohesperidin, pentadin, saccharin, sorbitol, *stevia* glycosides, sucralose, sucrose, tagatose, tryptophan, and xylitol. Formulations of the disclosure may have a sweetener content, in weight to weight (w/w) or weight to volume (w/v) proportions of the overall formulation, of 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 6%, 7%, 8%, 9%, or 10% or a range between any two of those sweetener content proportions. The formulations may comprise combinations of sweeteners, in amounts that individually or in aggregate achieve(s) the stated proportions.

In some embodiments, formulations of the disclosure can include a flavorant. Flavorants useful in the formulations of the present disclosure include chocolate, vanilla, caramel, orange, lemon, lime, strawberry, raspberry, blueberry, cherry, cinnamon, and nutmeg. Formulations of the disclosure may have a flavorant content, in weight to weight (w/w) or weight to volume (w/v) proportions of the overall formulation, of 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 6%, 7%, 8%, 9%, or 10% or in a range between two of those flavorant content proportions. The formulations may comprise combinations of flavorant, in amounts that individually or in aggregate achieve(s) the stated proportions.

In some embodiments, formulations of the disclosure can contain a pH adjusting agent and/or a buffer. Acidic pH adjusting agents useful in formulations of the disclosure include fumaric acid, formic acid, acetic acid, trichloroacetic acid, benzoic acid, oxalic acid, hydrofluoric acid, hydrogen sulfide, nitrous acid, sulfurous acid, phosphoric acid, and combinations thereof. Alkaline pH adjusting useful in formulations of the disclosure include sodium hydroxide, potassium hydroxide, calcium hydroxide, ammonium carbonate, ammonium hydroxide, ethanolamine, and trolamine. Buffers useful in formulations of the disclosure include acetic acid, sodium acetate, benzoic acid, sodium benzoate, boric acid, sodium borate, citric acid, sodium citrate, sodium phosphate, monobasic sodium phosphate, dibasic sodium phosphate, potassium phosphate, monobasic potassium phosphate, dibasic potassium phosphate, sodium acetate, lactic acid, a tartaric acid, sodium tartrate, sodium bicarbonate, sodium carbonate, tris (hydroxymethyl) aminomethane ("TRIS"), or a combination thereof. In such formulations, the buffer and/or pH adjusting agent are present in the formulations in amounts, alone or together, that are sufficient to cause the formulation to have a pH of from 6 to 11, for example pH 6, pH 6.1, pH 6.2, pH 6.3, pH 6.4, t pH 6.5, pH 6.6, pH 6.7, pH 6.8, pH 6.9, pH 7, pH 7.1, pH 7.2, pH 7.3, pH 7.4, pH 7.5, pH 7.6, pH 7.7, pH 7.8, pH 7.9, pH 8, pH 8.1, pH 8.2, pH 8.3, pH 8.4, pH 8.5, pH 8.6, pH 8.7, pH 8.8, pH 8.9, pH 9, pH 9.1, pH 9.2, pH 9.3, pH 9.4, pH 9.5, pH 9.6, pH 9.7, pH 9.8, pH 9.9, pH 10, pH 10.1, pH 10.2, pH 10.3, pH 10.4, pH 10.5, pH 10.6, pH 10.7, pH 10.8, pH 10.9, or pH 11 or in a range between two of those pH values.

In some embodiments, formulations of the present disclosure are pourable. The viscosities of such formulations can range from 1 centipoise ("cps") (i.e., the viscosity of water at room temperature) to 25,000 cps (i.e., the viscosity of chocolate syrup at room temperature); and exemplary particular viscosities of formulations of the disclosure include 1 cps, 25 cps, 50 cps, 75 cps, 100 cps, 150 cps, 200 cps (about the viscosity of maple syrup at room temperature), 250 cps, 300 cps, 400 cps, 500 cps, 600 cps, 700 cps, 800 cps, 900 cps, 1000 cps (about the viscosity of glycerin at room temperature), 1100 cps, 1200 cps, 1300 cps, 1400 cps, 1500 cps, 1600 cps, 1700 cps, 1800 cps, 1900 cps, 2000 cps, 2100 cps, 2200 cps, 2300 cps, 2400 cps, 2500 cps, 2600 cps, 2700 cps, 2800 cps, 2900 cps, 3000, 3500 cps, 4000 cps, 4500 cps, 5000 cps, 6000 cps, 7000 cps, 8000 cps, 9000 cps, 10,000 cps, 12,500 cps, 15,000 cps, 17,500 cps, 20,000, cps 22,500 cps, 25,000 cps (about the viscosity of chocolate syrup at room temperature), 27,500 cps, 30,000, cps as well as in a range between any two of said viscosities.

In some embodiments, formulations of the disclosure can contain a polymer. Non-ionic polymers useful in certain formulations of the disclosure include hydroxyethyl cellulose, hydroxypropylmethyl cellulose, methyl cellulose, carboxymethyl cellulose, polyvinyl pyrrolidone, and polyvinyl alcohol. Ionic polymers useful in certain formulations of the disclosure include polyacrylates (e.g., carbopols and carbomers), alginates, chitosans, hyaluronic acid, and xanthan gum. Formulations of the disclosure may have a ionic/nonionic polymer content, in weight to weight (w/w) or weight to volume (w/v) proportions of the overall formulation, of 0.001%, 0.005%, 0.01%, 0.05%, 0.1%, 0.25%, 0.5%, 0.75%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 6.0%, 7.0%, 8.0%, 9.0%, or 10.0% or in a range between two of those polymer content proportions. The formulations may comprise combinations of polymers, in amounts that individually or in aggregate achieve(s) the stated proportions.

In some embodiments, formulations of the disclosure contain a surfactant. Surfactants useful in certain formulations of the disclosure include sodium lauryl sulfate, docusate sodium, phosphatidylcholine, lecithin, betaines, tyloxapol, polyoxyethylene sorbitan esters, such as polysorbate 20, polysorbate 60, and polysorbate 80; polyethoxylated castor oils, such as cremaphor, polyethoxylated hydrogenated castor oils, such as HCO-40; and poloxamers. Formulations of the disclosure may have a surfactant content, in weight to weight (w/w) or weight to volume (w/v) proportions of the overall formulation, of 0.001%, 0.005%, 0.01%, 0.05%, 0.1%, 0.25%, 0.5%, 0.75%, 1.0%, 1.25%, 1.5%, 1.75%, 2.0%, 2.25%, 2.5%, 2.75%, 3.0%, 4.0%, or 5.0% or a range between two of those surfactant content proportions. The formulations may comprise combinations of surfactants, in amounts that individually or in aggregate achieve(s) the stated proportions.

In some embodiments, formulations of the disclosure can contain a tonicity agent. Ionic tonicity agents useful in certain formulations of the disclosure include calcium chloride, magnesium chloride, potassium chloride, sodium chloride, sodium sulfate, and combinations thereof. Nonionic tonicity agents useful in the formulations described herein include mannitol, sorbitol, xylitol, erythritol, lactitol, maltitol, isomalt, and combinations thereof. Formulations of the disclosure may have a tonicity agent content, in weight to weight (w/w) or weight to volume (w/v) proportions of the overall formulation, of 0.001%, 0.005%, 0.01%, 0.05%, 0.1%, 0.25%, 0.5%, 0.75%, 1.0%, 1.25%, 1.5%, 1.75%, 2.0%, 2.25%, 2.5%, 2.75%, 3.0%, 4.0%, or 5.0% or a range between two of those tonicity agent content proportions. The formulations may comprise combinations of tonicity agent, in amounts that individually or in aggregate achieve(s) the stated proportions.

In some embodiments, formulations of the disclosure can contain water. The formulations may have a water content, in weight to weight (w/w) or weight to volume (w/v) proportions of the overall formulation, of 6.0%, 6.5%, 7.0%, 7.5, 10%, 12.5, or 15% or in a range between two of those water content proportions.

In some embodiments, formulations of the disclosure can contain a preservative. Preservatives useful in certain formulations of the disclosure include dibutylhydroxytoluene, benzalkonium chloride, benzyl alcohol, borates, parabens (e.g., methylparaben and propylparaben), cresols, benzoic acid, phenol, sorbic acid, benzethonium chloride, sodium chlorite and combinations thereof. Formulations of the disclosure can have a preservative content, in weight to weight (w/w) or weight to volume (w/v) proportions of the overall formulation, of 0.001%, 0.005%, 0.01%, 0.05%, 0.1%, 0.25%, 0.5%, 0.75%, 1.0%, 1.25%, 1.5%, 1.75%, 2.0%, 2.25%, 2.5%, 2.75%, 3.0%, 4.0%, or 5.0% or in a range between two of those preservative content proportions. The formulations may comprise combinations of preservatives, in amounts that individually or in aggregate achieve(s) the stated proportions.

In any method for preparing a liquid formulation of topiramate as disclosed herein, if a suspension results from mixing of the topiramate with the glycerol, polyethylene glycol or mixture of them, the formulation can be heated to from 40° C. or above and not in excess of a temperature at which topiramate, PEG 400, and/or glycerol undergo thermal degradation such as 50° C., 55° C., 60° C., 65° C., 70° C., 75° C., 80° C., 85° C., 90° C., 95° C., 100° C., or 125° C., until a solution is obtained. The formulation is then preferably cooled to room temperature, a temperature of 25° C.±2° C.

EXAMPLES

Aspects of embodiments of the present disclosure may be further understood in light of the following examples, which should not be construed as limiting in any way. Formulations were evaluated for topiramate solubility, formulation viscosity, formulation assay and impurities over time to assess that the acceptability of the formulation. Objectives of the solubility and viscosity studies of the present disclosure were to evaluate the extent of topiramate stability in a variety of aqueous formulations.

Example 1

Topiramate solubility. Aqueous topiramate formulations C037-003, C037-005, C037-006, C037-008, C037-0018, C037-026, C037-027, C037-031, C037-038, C037-039, and C037-040 were prepared and comprised the ingredients set forth in Tables 1.1a and 1.1b and were studied in the topiramate stability experimental protocols described in this Example 1.

TABLE 1.1a

| | 2% w/w topiramate formulations | | | | | |
|---|---|---|---|---|---|---|
| Ingredient | C037C-003 | C037C-005 | C037C-006 | C037C-008 | C037C-0018 | C037C-026 |
| Topiramate | 2% w/w | 2% w/w | 2% w/w | 2% w/w | 2% w/w | 2% w/w |
| | 2.5% w/v | 2.5% w/v | 2.5% w/v | 2.5% w/v | 2.5% w/v | 2.5% w/v |
| | (25 mg/ml) | (25 mg/ml) | (25 mg/ml) | (25 mg/ml) | (25 mg/ml) | (25 mg/ml) |
| PEG 400 | 42% w/w | 42% w/w | 42% w/w | 58% w/w | 42% w/w | 58% w/w |
| | 50% w/v | 50% w/v | 50% w/v | 70% w/v | 50% w/v | 50% w/v |
| | (500 mg/ml) | (500 mg/ml) | (500 mg/ml) | (700 mg/ml) | (500 mg/ml) | (700 mg/ml) |
| Sucralose | 1% w/w | 1% w/w | 1% w/w | 1% w/w | 1% w/w | 1% w/w |
| | 1% w/v | 1% w/v | 1% w/v | 1% w/v | 1% w/v | 1% w/v |
| | (10 mg/ml) | (10 mg/ml) | (10 mg/ml) | (10 mg/ml) | (10 mg/ml) | (10 mg/ml) |
| Flavour berry | 0.2% w/w | 0.2% w/w | 0.2% w/w | 0.2% w/w | 0.2% w/w | 0.2% w/w |
| | 0.2% w/v | 0.2% w/v | 0.2% w/v | 0.2% w/v | 0.2% w/v | 0.2% w/v |
| | (2 mg/ml) | (2 mg/ml) | (2 mg/ml) | (2 mg/ml) | (2 mg/ml) | (2 mg/ml) |

TABLE 1.1a-continued

| | 2% w/w topiramate formulations | | | | | |
|---|---|---|---|---|---|---|
| Ingredient | C037C-003 | C037C-005 | C037C-006 | C037C-008 | C037C-0018 | C037C-026 |
| Water | 0% w/w | 4% w/w | 8% w/w | 8% w/w | 1% w/w | 5% w/w |
| | 0% w/v | 5% w/v | 10% w/v | 10% w/v | 1% w/v | 6% w/v |
| | (0 mg/ml) | (50 mg/ml) | (100 mg/ml) | (100 mg/ml) | (10 mg/ml) | (60 mg/ml) |
| Glycerol | q.s. ad 1 ml | q.s. ad 1 ml | q.s. ad 1 ml | q.s. ad 1 ml | q.s. ad 1 ml | q.s. ad 1 ml |
| | ~55% w/w | ~51% w/w | ~47% w/w | ~30% w/w | ~54% w/w | ~34% w/w |
| | (663 mg/ml) | (613 mg/ml) | (563 mg/ml) | (363 mg/ml) | (653 mg/ml) | (403 mg/ml) |

TABLE 1.1b

| | 2% w/w topiramate formulations | | |
|---|---|---|---|
| Ingredient | C037-031 | C037-027<br>C037-032<br>C037-039<br>C037-040 | C037-038 |
| Topiramate | 4% w/w | 4% w/w | 4% w/w |
| | 5% w/v | 5% w/v | 5% w/v |
| | (50 mg/ml) | (50 mg/ml) | (50 mg/ml) |
| PEG 400 | 42% w/w | 42% w/w | 25% w/w |
| | 50% w/v | 50% w/v | 30% w/v |
| | (500 mg/ml) | (500 mg/ml) | (300 mg/ml) |
| Sucralose | 1% w/w | 1% w/w | 1% w/w |
| | 1% w/v | 1% w/v | 1% w/v |
| | (10 mg/ml) | (10 mg/ml) | (10 mg/ml) |
| Flavour berry | 0.2% w/w | 0.2% w/w | 0.2% w/w |
| | 0.2% w/v | 0.2% w/v | 0.2% w/v |
| | (2 mg/ml) | (2 mg/ml) | (2 mg/ml) |
| Water | 0% w/w | 5% w/w | 0% w/w |
| | 0% w/v | 6% w/v | 0% w/v |
| | (0 mg/ml) | (60 mg/ml) | (0 mg/ml) |
| Glycerol | q.s. ad 1 ml | q.s. ad 1 ml | q.s. ad 1 ml |
| | ~48% w/w | ~53% w/w | ~64% w/w |
| | (578 mg/ml) | (638 mg/ml) | (838 mg/ml) |

Topiramate batch manufacture. Formulations C037-003, C037-005, C037-006, C037-008, C037-0018, C037-026, C037-027, C037-031, C037-032, C037-038 C037-039, and C037-040 were made as follows. At room temperature (i.e., 25° C.±2° C.) the amounts of topiramate, PEG 400, sucralose, berry flavor, water, and glycerol required for planned batch size to be manufactured (e.g., for purposes of analyzing each formulation in the topiramate HPLC assay at the specified time points) were independently weighed on a laboratory scale. Such amount of the PEG 400 was transferred to a stainless-steel vessel, to which the topiramate was slowly added under continuous stirring at room temperature (i.e., 25° C.±2° C.). To the resultant liquids, sucralose, water, and/or glycerol were added under continued stirring at room temperature (i.e., 25° C.±2° C.) to form the formulations. The formulations were subsequently stored at room temperature (i.e., 25° C.±2° C.). Some of the formulation may contains parabens i.e. methyl paraben and propyl paraben (total not more than 3% w/v) and the amount compensated with glycerol.

Topiramate HPLC analytical testing. HPLC analytical testing (see infra) of formulations C037-003, C037-005, C037-006, C037-008, C037-0018, C037-026, C037-027, C037-031, C037-032, C037-038, C037-039 and C037-040 was conducted after 0, 1, 2, 3, 6, and/or 9 months storage at 25° C. or 40° C. and 60% relative humidity ("RH") or 75% RH, as specified in Tables 1.5a and 1.5b. 10 ml of each formulation was analyzed for topiramate, related compound A, maximum impurity, and D-fructose content by the methods described below.

The analytical methods and sampling steps performed on formulations C037-003, C037-005, C037-006, C037-008, C037-0018, C037-026, C037-027, C037-031, C037-032, C037-038, C037-039 and C037-040 were conducted as set forth in Table 1.2, at room temperature (25° C.±2° C.) and.

TABLE 1.2

| Time point | Analytical methods and sampling steps |
|---|---|
| Initial | a. 10 ml samples were collected from each of bulk formulations C037-003, C037-005, C037-006, C037-008, C037-0018, C037-026, C037-027, C037-031, C037-038, and C037-040, promptly after manufacture.<br>b. The topiramate HPLC assay was performed on each sample collected in Initial Time point of step a. The topiramate, topiramate-related compound A, maximum impurity, and D-fructose concentrations (in mg/ml) of each sample was determined. |
| 1 M | a. 10 ml samples were collected from each of the bulk formulations C037-003, C037-005, C037-006, C037-008, C037-0018, C037-026, C037-027, C037-031, C037-038, and C037-040, 1 month (i.e., 30 days) after manufacture.<br>b. The topiramate HPLC assay was performed on each sample collected in $T_{1\ day}$ step a. The topiramate, topiramate-related compound A, maximum impurity, and D-fructose concentrations (in mg/ml) of each sample was determined. |
| 2 M | a. 10 ml samples were collected from each of the bulk formulations C037-003, C037-005, C037-006, C037-008, C037-0018, C037-026, C037-027, C037-031, C037-038, and C037-040, two months (i.e., 60 days) after manufacture.<br>b. The topiramate HPLC assay was performed on each sample collected in 2 M step<br>a. The topiramate, topiramate-related compound A, maximum impurity, and D-fructose concentrations (in mg/ml) of each sample was determined. |
| 3 M | a. 10 ml samples were collected from each of the bulk formulations C037-003, C037-005, C037-006, C037-008, C037-0018, C037-026, C037-027, C037-031, C037-038, and C037-040, three months (i.e., 90 days) after manufacture. |

TABLE 1.2-continued

| Time point | Analytical methods and sampling steps |
|---|---|
| | b. The topiramate HPLC assay was performed on each sample collected in 3 M step<br>  a. The topiramate, topiramate-related compound A, maximum impurity, and D-fructose concentrations (in mg/ml) of each sample was determined. |
| 6 M | a. 10 ml samples were collected from each of the bulk formulations C037-003, C037-005, C037-006, C037-008, C037-0018, C037-026, C037-027, C037-031, C037-038, and C037-040, six months (i.e., 180 days) after manufacture.<br>b. The topiramate HPLC assay was performed on each sample collected in 3 M step<br>  a. The topiramate, topiramate-related compound A, maximum impurity, and D-fructose concentrations (in mg/ml) of each sample was determined. |
| 9 M | a. 10 ml samples were collected from each of the bulk formulations C037-003, C037-005, C037-006, C037-008, C037-0018, C037-026, C037-027, C037-031, C037-038, and C037-040, nine months (i.e., 270 days) after manufacture.<br>b. The topiramate HPLC assay was performed on each sample collected in 3 M step<br>  a. The topiramate, topiramate-related compound A, maximum impurity, and D-fructose concentrations (in mg/ml) of each sample was determined. |

The solutions, standards, and samples used in the topiramate assay analytical methods of the present disclosure were as described in Table 1.2.

TABLE 1.2

Topiramate assay solutions

| | |
|---|---|
| Water | HPLC grade (e.g., MilliQ or equivalent) |
| Column wash | HPLC grade acetonitrile (e.g., Merck or J T Baker) and water (60:40 v/v) |
| Mobile phase | Acetonitrile and water (60:40 v/v) |
| Diluent | Acetonitrile and water (50:50) |
| Assay standard solution | 2 mg/mL topiramate RS in mobile phase |
| Assay sample solution | 2 mg/mL topiramate RS in mobile phase |
| Assay system suitability solution | 0.02 mg/mL each of fructose RS and USP topiramate related compound A RS in the sample solution |

The chromatographic conditions for the topiramate high performance liquid chromatography ("HPLC") assay employed in the present disclosure were as forth in Table 1.3.

TABLE 1.3

Topiramate Assay HPLC system

| Chromatographic parameters | Equipment and/or conditions |
|---|---|
| System | HPLC-RI |
| Detector | Refractive index |
| Elution mode | Isocratic |
| Column | 4.6-mm × 25-cm; 5-μm packing L1 (Inertsil ODS 250 × 4.6 mm, 5 μm) |
| Column temperature | 50° C. |
| Sampler temperature | 25° C. |
| Detector temperature | 55° C. |
| Flow Rate | 0.6 ml/min |
| Polarity | Positive |
| Injection volume | 50 μl |
| Topiramate retention time | 12 to 13 minutes |
| Run Time | Not less than 3 times the topiramate retention time |

Standard solutions I & II preparation. 50 mg of topiramate was weighed and transferred into a 50 ml volumetric flask, to which 20 ml diluent was added and sonicated until dissolved. The resultant solution was mixed well and diluted with the same diluent until 1000 μg/ml of topiramate was attained. Preparation of standard solution II was the same as for standard solution I.

Sample solution preparation. 1.0 g of sample supernatant was weighed and transferred into 25 ml volumetric flask, to which 15 ml diluent was added, vigorously shaken for 5 minutes, and sonicated for 5 minutes. The resultant solution was with the same diluent until 1000 μg/ml of topiramate was achieved. Note: topiramate HPLC assay samples were prepared in duplicate and run through the HPLC assay. Their average value was reported.

Topiramate HPLC assay procedure. The HPLC system was equilibrated with mobile phase. Iterative injections of diluent were made until a clean and reproducible baseline was achieved. The chromatograms were recorded and any peak eluting at the retention time of major peaks identified. Five replicate injections of topiramate standard solution I and two replicate injections of topiramate standard solution II were made and chromatograms recorded. The sample solution was injected (in duplicate) and topiramate content calculated in terms of percentage with equations provided in Table 1.4.

The equation employed to calculate percent assay for topiramate in the samples of the formulations of the present disclosure are set forth in Table 1.4.

TABLE 1.4

Topiramate HPLC assay equations $$\text{Assay for topiramate} = \frac{Aspl}{Astd} \times \frac{Wstd(\text{mg})}{50 \text{ mL}} \times \frac{25 \text{ mL}}{Wspl(\text{mg})} \times \frac{P(\%)}{100} \times \text{Wt./mL}$$

Percent assay $$\% \text{ Assay} = \frac{\text{Assay}(\text{mg/ml})}{LC(\text{mg/ml})} \times 100$$

Where:
Astd  Average area response of five replicate injections for topiramate in standard solution I
Aspl  Average area response of topiramate obtained in the sample solution
Wstd  Weight of the topiramate working standard taken in mg
Wspl  Weight of sample in mg
P  Purity of topiramate working standard on as is basis in percentage
L  Label claim of topiramate in mg/mL
Wt/ml  Weight per ml in g/ml The topiramate HPLC assay experimental results for formulations C037-003, C037-005, C037-006, C037-008, C037-0018, C037-026, C037-027, C037-031, C037-038, and C037-040 are reported in Tables 1.5a and 1.5b.

TABLE 1.5a

| Formulation: | Sample condition | % Related Substances ||| Total impurities | % Assay |
| | | Related compound A* | Single maximum impurity♦ | D-fructoseΔ | | |
|---|---|---|---|---|---|---|
| C037-003 | Initial | ND□ | ND | ND | ND | 99.9 |
| | 1 M 40° C./75% RH | ND | ND | ND | ND | 102.2 |
| | 2 M 40° C./75% RH | ND | ND | ND | ND | 98.4 |
| | 3 M 40° C./75% RH | 0.27 | ND | ND | 0.27 | 97.0 |
| | 6 M 40° C./75% RH | 0.56 | ND | ND | 0.56 | 96.9 |
| | 6 M 25° C./60% RH | 0.06 | ND | ND | 0.06 | 100.3 |
| | 9 M 25° C./60% RH | 0.06 | ND | ND | 0.06 | 101.3 |
| C037-005 | Initial | ND | ND | ND | ND | 97.7 |
| | 1 M 40° C./75% RH | ND | ND | ND | ND | 98.9 |
| | 2 M 40° C./75% RH | 0.23 | ND | ND | 0.23 | 98.7 |
| | 3 M 40° C./75% RH | 0.43 | ND | ND | 0.43 | 97.7 |
| | 6 M 40° C./75% RH | 1.03 | ND | ND | 1.03 | 95.5 |
| | 6 M 25° C./60% RH | 0.09 | ND | ND | 0.09 | 98.9 |
| | 9 M 25° C./60% RH | 0.098 | ND | ND | 0.098 | 101.5 |
| C037-006 | Initial | ND | ND | ND | ND | 99.8 |
| | 1 M 40° C./75% RH | ND | ND | ND | ND | 101.4 |
| | 2 M 40° C./75% RH | 0.37 | ND | ND | 0.37 | 99.7 |
| | 3 M 40° C./75% RH | 0.57 | ND | ND | 0.57 | 98.9 |
| | 6 M 40° C./75% RH | 1.38 | ND | ND | 1.38 | 96.7 |
| | 6 M 25° C./60% RH | 0.13 | ND | ND | 0.13 | 101.4 |
| | 9 M 25° C./60% RH | 0.16 | ND | ND | 0.16 | 101.0 |
| C037-008 | Initial | ND | ND | ND | ND | 99.0 |
| | 1 M 40° C./75% RH | ND | ND | ND | ND | 98.7 |
| | 2 M 40° C./75% RH | 0.29 | ND | ND | 0.29 | 98.6 |
| | 3 M 40° C./75% RH | 0.47 | ND | ND | 0.47 | 97.1 |
| | 6 M 40° C./75% RH | 1.02 | ND | ND | 1.02 | 95.5 |
| | 6 M 25° C./60% RH | 0.13 | ND | ND | 0.13 | 99.0 |
| | 9 M 25° C./60% RH | 0.10 | ND | ND | 0.10 | 98.6 |
| C037-018 | Initial | ND | ND | ND | ND | 98.9 |
| | 1 M 40° C./75% RH | ND | ND | ND | ND | 98.3 |
| | 3 M 40° C./75% RH | 0.41 | ND | ND | 0.41 | 98.5 |
| | 6 M 40° C./75% RH | 0.72 | ND | ND | 0.72 | 96.3 |
| | 6 M 25° C./60% RH | 0.05 | ND | ND | 0.05 | 100.3 |
| C037-026 | Initial | ND | ND | ND | ND | 102.7 |
| | 3 M 25° C./60% RH | ND | ND | ND | ND | 100.3 |
| C037-027 | Initial | ND | ND | ND | ND | 101.0 |
| | 3 M 25° C./60% RH | ND | ND | ND | ND | 100.2 |
| C037-031 | Initial | 0.03 | ND | ND | 0.03 | 100.5 |
| | 3 M 25° C./60% RH | 0.04 | ND | ND | 0.04 | 98.9 |
| C037-032 | Initial | 0.03 | ND | ND | 0.03 | 99.8 |
| | 3 M 25° C./60% RH | 0.04 | ND | ND | 0.04 | 98.3 |

*Limit not more than 0.5%;
♦Limit not more than 0.2%;
ΔLimit not more than 0.3%;
□Not Detected TABLE 1.5b

| Formulation | Sample condition | % Related Substances ||| Total impurities | % Assay |
| | | Related compound A* | Single maximum impurity♦ | D-fructoseΔ | | |
|---|---|---|---|---|---|---|
| C037-003 | Initial | ND□ | ND | ND | ND | 99.6 |
| | 70° C. - 24 hrs[#] | 0.60 | ND | ND | 0.60 | 99.7 |
| | 70° C. - 48 hrs[#] | 0.70 | ND | ND | 0.70 | 98.0 |
| C037-038 | Initial | ND | ND | ND | ND | 101.6 |
| | 70° C. - 24 hrs[#] | 0.46 | ND | ND | 0.46 | 99.8 |
| | 70° C. - 48 hrs[#] | 0.62 | ND | ND | 0.62 | 99.9 |
| | Initial | ND | ND | ND | ND | 101.6 |
| | 70° C. - 24 hrs[##] | 0.46 | ND | ND | 0.46 | 100.7 |
| | 70° C. - 48 hrs[##] | 0.66 | ND | ND | 0.66 | 101.2 |
| C037-039 | Initial | ND | ND | ND | ND | 98.6 |
| | 70° C. - 24 hrs[#] | 0.56 | ND | ND | 0.56 | 99.8 |
| | 70° C. - 48 hrs[#] | 0.83 | ND | ND | 0.82 | 99.9 |
| | Initial | ND | ND | ND | ND | 98.6 |
| | 70° C. - 24 hrs[##] | 0.58 | ND | ND | 0.58 | 99.7 |
| | 70° C. - 48 hrs[##] | 0.85 | ND | ND | 0.85 | 99.3 |

TABLE 1.5b-continued

| Formulation | Sample condition | % Related Substances | | | Total impurities | % Assay |
|---|---|---|---|---|---|---|
| | | Related compound A* | Single maximum impurity♦ | D-fructoseΔ | | |
| C037-040 | Initial | ND | ND | ND | ND | 100.0 |
| | 70° C. - 24 hrs# | 0.58 | ND | ND | 0.58 | 99.7 |
| | 70° C. - 48 hrs# | 0.85 | ND | ND | 0.85 | 99.3 |
| | Initial | ND | ND | ND | ND | 100.0 |
| | 70° C. - 24 hrs## | 0.58 | ND | ND | 0.58 | 99.5 |
| | 70° C. - 48 hrs## | 0.84 | ND | ND | 0.84 | 99.4 |

*Limit not more than 0.5%;
♦Limit not more than 0.2%;
ΔLimit not more than 0.3%;
▫Not Detected
Packed in glass bottles,
packed in glass bottles with added PIBA components As can be seen, aqueous topiramate formulations of the present disclosure exhibit insignificant assay drop (i.e., the difference in the initial topiramate % assay value and: (i) the 1-, 2-, 3-, 6-, or 9-month topiramate percent assay value at 40° C./75% RH or 25° C./60% RH, or (ii) the 24 hour or 48 hour topiramate percent assay value at 70° C.) when stored exposed to standard atmospheric oxygen. In particular without manipulation such as replacing standard atmospheric gas mixtures with inert and oxygen-free gas like nitrogen or argon.

Furthermore, aqueous topiramate formulations of the present disclosure exhibit insignificant topiramate-related compound A increase (i.e., the difference in topiramate related compound A percent value and: (i) the 1-, 2-, 3-, 6-, or 9-month topiramate-related compound A percent value at 40° C./75% RH or 25° C./60% RH, or (ii) the 24 hour or 48 hour topiramate-related compound A percent value at 70° C.) when stored exposed to standard atmospheric oxygen. In particular, without manipulation such as replacing standard atmospheric gas mixtures with inert and oxygen-free gas like nitrogen or argon It follows that topiramate formulations provided by the present disclosure possess unexpectedly advantageous storage stability properties.

In some embodiments, topiramate formulations of the present disclosure exhibit a topiramate assay drop of 0%, 1%, 2%, 3%, 4%, 5%, 6%, 7%, 8%, 9%, or 10% or ranges between any two of those topiramate assay drop values when stored at 40° C./75% RH or 25° C./60% RH for 1, 2, 3, 4, 5, 6, 9, 12, 18, 24, or 36 months (or a range between any two of those monthly time periods) exposed to standard atmospheric oxygen. In particular, without manipulation such as replacing standard atmospheric gas mixtures with inert and oxygen-free gas like nitrogen or argon In some embodiments, topiramate formulations of the present disclosure exhibit a topiramate-related compound A increase of 0%, less than 0.5%, 0.5%, 0.6%, 0.7%, 0.8%, 0.9%, 1%, 1.25%, 1.5%, 1.75%, or 2% or ranges between any two of those topiramate-related compound A increase values when stored at 40° C./75% RH or 25° C./60% RH for 1, 2, 3, 4, 5, 6, 9, 12, 18, 24, or 36 months (or a range between any two of those monthly time periods) exposed to standard atmospheric oxygen. In particular, without manipulation such as replacing standard atmospheric gas mixtures with inert and oxygen-free gas like nitrogen or argon.

While the foregoing specification teaches the principles of the present invention, with examples provided for the purpose of illustration, it will be understood that the practice of the invention encompasses all variations, adaptations and/or modifications as come within the scope of the following claims and their equivalents.

What is claimed is:

1. An aqueous pharmaceutical formulation, suitable for oral administration, comprising:
   from 2% w/v to 7.5% w/v topiramate or a pharmaceutically acceptable salt thereof;
   from 45% w/v to 75% w/v polyethylene glycol 400;
   from 7.5% w/v to 12% w/v water; and
   balance glycerol,
wherein the formulation exhibits a topiramate assay drop of 2% to 10% after six months at 40° C. and 75% relative humidity.

2. The formulation of claim 1, wherein the topiramate assay drop is from 2% to 7.5%.

3. The formulation of claim 2, wherein the formulation further comprises one or more of 0.01% w/v to 2.0% w/v sucralose and 0.01% w/v to 2.0% w/v of a berry flavorant.

4. The formulation of claim 3, wherein the formulation further comprises one or more of 1% w/v to 5.0% w/v methylparaben and 0.01% w/v to 1.0% w/v propylparaben.

5. A method of treating one or more of conditions: (i) partial-onset tonic-clonic seizures, (ii) primary generalized tonic-clonic seizures, or (iii) seizures associated with Lennox-Gastaut syndrome, comprising orally administering the formulation of claim 1 to a subject presenting one or more of conditions (i), (ii), and (iii).

6. An aqueous pharmaceutical formulation, suitable for oral administration, comprising:
   2.5% w/v or 5% w/v topiramate or a pharmaceutically acceptable salt thereof;
   50% w/v or 70% w/v polyethylene glycol 400;
   7.5% w/v, 8% w/v, 10% w/v, or 12% w/v water; and
   balance glycerol,
   wherein the formulation exhibits a topiramate-related compound A increase of 0.5% to 2% after six months at 40° C. and 75% relative humidity.

7. The formulation of claim 6, wherein the topiramate related compound A increase is 1% to 2%.

8. The formulation of claim 7, wherein the formulation further comprises one or more of 0.01% w/v to 2.0% w/v sucralose and 0.01% w/v to 2.0% w/v of a berry flavorant.

9. The formulation of claim 8, wherein the formulation further comprises one or more of 1% w/v to 5.0% w/v methylparaben and 0.01% w/v to 1.0% w/v propylparaben.

10. A method of treating one or more of conditions: (i) partial-onset tonic-clonic seizures, (ii) primary generalized tonic-clonic seizures, or (iii) seizures associated with Lennox-Gastaut syndrome, comprising orally administering the formulation of claim 6 to a subject presenting one or more of conditions (i), (ii), and (iii).

11. The formulation of claim 1 comprising from 8% w/v to 12% w/v water.

12. The formulation of claim 1 comprising from 10% w/v to 12% w/v water.

13. The formulation of claim 1 comprising from 7.5% w/v to 10% w/v water.

14. The formulation of claim 1 comprising from 8% w/v to 10% w/v water.

15. The formulation of claim 1 comprising 7.5% w/v water.

16. The formulation of claim 1 comprising 8% w/v water.

17. The formulation of claim 1 comprising 10% w/v water.

18. The formulation of claim 1 comprising 12% w/v water.

\* \* \* \* \*